(12) United States Patent
Schreiber et al.

(10) Patent No.: US 11,065,013 B2
(45) Date of Patent: Jul. 20, 2021

(54) POSITIONING DEVICE FOR FIXING A POLY AXIAL PLATE IN A TUBULAR BONE

(71) Applicant: OT MEDIZINTECHNIK GMBH, München (DE)

(72) Inventors: Ulrich Schreiber, Munich (DE); Lukas Zapf, Munich (DE); Johannes Gattinger, Landshut (DE)

(73) Assignee: OT MEDIZINTECHNIK GMBH, Munich (DE)

(*) Notice: Subject to any disclaimer, the term of this patent is extended or adjusted under 35 U.S.C. 154(b) by 81 days.

(21) Appl. No.: 16/081,224

(22) PCT Filed: Mar. 1, 2017

(86) PCT No.: PCT/EP2017/054798
§ 371 (c)(1),
(2) Date: Jan. 17, 2019

(87) PCT Pub. No.: WO2017/149026
PCT Pub. Date: Sep. 8, 2017

(65) Prior Publication Data
US 2019/0133611 A1    May 9, 2019

(30) Foreign Application Priority Data

Mar. 1, 2016   (DE) .................... 10 2016 103 681.1
Mar. 2, 2016   (DE) .................... 10 2016 103 754.0

(51) Int. Cl.
*A61B 17/17*   (2006.01)
*A61B 17/80*   (2006.01)

(52) U.S. Cl.
CPC ........ *A61B 17/1728* (2013.01); *A61B 17/808* (2013.01)

(58) Field of Classification Search
CPC ................... A61B 17/1728; A61B 17/808
See application file for complete search history.

(56) References Cited

U.S. PATENT DOCUMENTS

2004/0102788 A1* 5/2004 Huebner ............ A61B 17/1728
                                                    606/96
2006/0264942 A1* 11/2006 Lim .................. A61B 17/7031
                                                    606/254

(Continued)

FOREIGN PATENT DOCUMENTS

DE          20013900 U1    6/2001
DE     102006016213 A1    10/2007

(Continued)

OTHER PUBLICATIONS

International Search Report for PCT/EP2017/054798 dated Oct. 30, 2017.

(Continued)

*Primary Examiner* — Matthew J Lawson
*Assistant Examiner* — Lisa Nguyen
(74) *Attorney, Agent, or Firm* — Millman IP Inc.

(57) ABSTRACT

A positioning device is provided, having a guiding bow, wherein the guiding bow at least in section thereof is designed as or comprises a push-in section to be inserted into a sleeve of a push-in sleeves arrangement; wherein the guiding bow comprises or is connected to an adjusting device, wherein the adjusting device comprises at least one targeting device, and wherein the targeting device is designed to receive, at least in section, an interlocking device or an instrument for acting on the interlocking device.

15 Claims, 11 Drawing Sheets

(56) References Cited

U.S. PATENT DOCUMENTS

| | | | |
|---|---|---|---|
| 2007/0173836 A1 | 7/2007 | Prien | |
| 2007/0173843 A1* | 7/2007 | Matityahu | A61B 17/80 606/916 |
| 2008/0188852 A1* | 8/2008 | Matityahu | A61B 17/1728 606/54 |
| 2011/0106086 A1* | 5/2011 | Laird | A61B 17/1728 606/70 |
| 2018/0256222 A1* | 9/2018 | Lueth | A61B 17/809 |
| 2020/0352582 A1* | 11/2020 | Larche | A61B 17/8019 |
| 2020/0388085 A1* | 12/2020 | Furnstahl | A61B 17/808 |

FOREIGN PATENT DOCUMENTS

| | | |
|---|---|---|
| DE | 10 2014 109935 A1 | 1/2016 |
| EP | 2 745 786 A2 | 6/2014 |
| ES | 2 523 021 T3 | 11/2014 |
| WO | 2016008849 A1 | 1/2016 |

OTHER PUBLICATIONS

English translation of search report for German application No. 10 2016 103 681.1 dated Oct. 7, 2016.

\* cited by examiner

POSITIONING DEVICE FOR FIXING A POLY AXIAL PLATE IN A TUBULAR BONE

The present invention relates to a positioning device for the plate osteosynthesis according to the preamble of claim 1, further to a push-in sleeves arrangement according to the preamble of claim 17.

Plates are known aids for the treatment of fractures of e.g. long tubular bones, but also of other bones. They are connected to bones by screws.

In hitherto known plates, the screws are screwed in the bone through discrete openings of the plate in a predetermined position relative to the plate. The exact placing of the screws in the bone requires a great experience by the surgeon.

It is an object of the present invention to provide a positioning device for fixing a plate to a bone or the bone to a plate. Furthermore, a push-in sleeves arrangement should be specified.

The object according to the present invention is achieved with a positioning device having the features of claim 1. It is further achieved with a push-in sleeves arrangement having the features of claim 17.

The positioning device serves for positioning and/or fixing a plate to a bone. It comprises a guiding bow. The guiding bow is designed at least in one section thereof as a push-in section to be inserted in a sleeve of a push-in sleeves arrangement, comprises such a push-in section or is connected thereto.

The guiding bow comprises or is connected to an adjusting device, wherein the adjusting device comprises at least one targeting device. The targeting device is designed to receive, at least in section, an interlocking device or an instrument for acting on the interlocking device.

The push-in sleeves arrangement according to the present invention comprises at least one or a plurality of sleeves for the insertion of the push-in section of a positioning device therein, in particular the positioning device according to the present invention.

In all of the following statements, the use of the expression "may be" or "may have" and so on, is to be understood synonymously with "preferably is" or "preferably has," and so on respectively, and is intended to illustrate embodiments according to the present invention.

Whenever numerical words are mentioned herein, the person skilled in the art shall recognize or understand them as indications of numerical lower limits. Hence, unless it leads to a contradiction evident for the person skilled in the art, the person skilled in the art shall comprehend for example "one" as encompassing "at least one". This understanding is also equally encompassed by the present invention as the interpretation that a numeric word, for example, "one" may alternatively mean "exactly one", wherever this is evidently technically possible in the view of the person skilled in the art. Both of these understandings are encompassed by the present invention and apply herein to all used numerical words.

Advantageous developments of the present invention are each subject-matter of the dependent claims and embodiments.

In several exemplary embodiments according to the present invention, the push-in section is, or comprises, a push-in rod.

In several exemplary embodiments according to the present invention, the positioning device comprises a push-in sleeves arrangement which comprises a plurality of sleeves for inserting the push-in section into them.

In several exemplary embodiments according to the present invention, at least two of the sleeves comprise each a longitudinal axis. Not each of these longitudinal axes are parallel to each other.

The positioning device may in several exemplary embodiments according to the present invention be referred to as monoaxial, when or if the positioning device is designed or arranged for introducing the interlocking device, e.g. a bone screw, into the particular through-opening of the plate at only one angle.

In several exemplary embodiments according to the present invention, the push-in sleeves arrangement comprises a plate holder connected thereto. The plate holder extends preferably from the push-in sleeves arrangement.

In several exemplary embodiments according to the present invention, the plate holder comprises a first connection via which the plate holder is connected or connectable to a further section of the push-in sleeves arrangement in a releasable manner.

In several exemplary embodiments according to the present invention, the plate holder comprises a second connection for connecting it to a plate for osteosynthesis.

In several exemplary embodiments according to the present invention, the first and/or the second connection is designed as, or comprises, a screw connection. The first connection and/or the second connection may be a combination of several connection mechanisms, e.g. screw connections and push-in connections at the same time.

The plate may be designed as polyaxial or monoaxial or as a combination thereof. The same may apply to the positioning device according to the present invention.

"Polyaxial" may be understood such that the positioning device which is connected to the plate is designed or arranged for inserting the interlocking device, e.g. a bone screw, into a particular through-opening at a plurality of angles, also called multidirectional.

"Monoaxial" may be understood such that the positioning device which is connected to the plate is designed or arranged for inserting the interlocking device, e.g. a bone screw, into a particular through-opening of the plate at only one angle.

The plate may in several exemplary embodiments according to the present invention be referred to as polyaxial, when or if the positioning device is designed or arranged to insert the interlocking device, e.g. a bone screw, into the particular through-opening at more than only one angle.

In several exemplary embodiments according to the present invention, the push-in section comprises at least one guiding pin extending radially therefrom. The guiding pin serves for guiding the push-in section within a sleeve being selected from the plurality of sleeves. Said guiding may optionally take place along a longitudinal groove (also referred to as groove) provided in each of the sleeves.

In several exemplary embodiments according to the present invention, each of the plurality of sleeves comprises at least one longitudinal groove.

In several exemplary embodiments according to the present invention, the arrangement of the sleeves and the arrangement of the push-in section are interchanged with each other. The push-in section may thus be placed or located on the component denoted as push-in sleeves arrangement and the sleeve or the sleeves may be placed on the positioning device.

In several exemplary embodiments according to the present invention, the longitudinal groove does not extend along the total length of the sleeve. This may ensure that the insertion may be limited upon inserting the push-in section into the sleeve. Additionally or alternatively, the width of the longitudinal groove is not constant over or along the total length of the sleeve. This may allow the guiding pin to jam or engage in an end section of the groove, ensuring for example a deadlock or clamping, an optimal positioning of the guiding bow relative to the sleeve and/or to the plate.

In several exemplary embodiments according to the present invention, the longitudinal groove extends at least in section also in the circumferential direction of the sleeve. This may advantageously allow that the push-in section interlocks with the sleeve and/or prevent that the push-in section slips out of the sleeve unintentionally.

In several exemplary embodiments according to the present invention, the longitudinal groove comprises at least one fitting section which provides a predetermined fit with the guiding pin.

In several exemplary embodiments according to the present invention, the longitudinal groove comprises the at least one fitting section in an end section of the longitudinal groove or in a region in which a guiding pin should rest after having inserted the push-in section into the sleeve. The remaining sections of the longitudinal groove are wider than the fitting section. Thus, the guiding section may be easily inserted into the longitudinal groove and takes the snug fit only when the insertion is about to be completed.

In several exemplary embodiments according to the present invention, the cross-sectional shape of the sleeve is oval, rectangular, non-annular, angular, triangular, etc.

In several exemplary embodiments according to the present invention, the cross-sectional shape of the sleeve (oval, rectangular, non-annular, angular, triangular, etc.) is designed such that the axis and the alignment of the guiding pin and hence of the guiding bow are determined around or about this axis.

In several exemplary embodiments according to the present invention, the height limit or limitation of the guiding pin and thus of the guiding bow along the axis of the sleeve and thus of the guiding pin is determined via a fitting at the front/end side of the sleeve relative to or vis-à-vis a step of the guiding pin.

In several exemplary embodiments according to the present invention, the height limit of the guiding pin and thus of the guiding bow along the axis of the sleeve and thus of the guiding pin is determined via a fitting at the front/end side of the sleeve relative to or vis-à-vis a step which is shiftable or adjustable in axial direction.

In several exemplary embodiments according to the present invention, the height limit of the guiding pin and thus of the guiding bow is determined between guiding pin and sleeve along the axis of the sleeve and thus of the guiding pin through a fitting on the front/end side of the sleeve relative to a spacer between guiding pin and sleeve with different lengths.

In several exemplary embodiments according to the present invention, the plurality of sleeves is denoted by markings on the push-in sleeves arrangement. This designation may specify which opening or through-opening of the plates the interlocking device which is received in the targeting device of the adjusting device is directed to or aligned with. This may facilitate work for the surgeon. Sleeves and opening or through-opening may be uniquely or unambiguously marked so that an alignment or attribution 2 of a particular sleeve is possible to—preferably only—one particular through-opening.

The markings on the plate may be designed to be read or recognized by screening or x-ray.

In several exemplary embodiments according to the present invention, the plurality of sleeves is screwed to other sections of the push-in sleeves arrangement, is connected by fitting, by gluing and/or by dowel pin.

In several exemplary embodiments according to the present invention, each of the plurality of sleeves has at least one opening for at least one dowel pin.

In several exemplary embodiments according to the present invention, the push-in section comprises in its outer surface or shell surface a through-opening for guiding through a guiding pin. The push-in section comprises in an interior thereof at least one longitudinal opening, wherein in the interior or in the longitudinal opening a rod is rotatably arranged carrying on its outer surface the guiding pin or from which the guiding pin protrudes, wherein the guiding pin is led through the through-opening.

In several exemplary embodiments according to the present invention, the sleeve comprises, e.g. in its outer surface or shell surface, at least one or exactly one guide or dowel pin as rotation-proof or as anti-twist safeguard. The push-in section may comprise at least one groove or longitudinal opening.

In several exemplary embodiments according to the present invention, the rod comprises a hand element for turning the rod by hand within the longitudinal opening of the push-in section.

In several exemplary embodiments according to the present invention, the positioning device is connected to the push-in sleeves arrangement. The push-in sleeves arrangement is in turn connected to a plate for osteosynthesis. The plate comprises a plurality of openings or through-openings for receiving one or several interlocking devices. The depth of the through-openings respectively corresponds to a thickness of the plate at the location of the through-opening. Among the plurality of sleeves there is at least one that corresponds to one or to several of the through openings. The adjusting device is designed such if the push-in section—preferably having, if provided, an interlocked guiding pin—is inserted into one of the sleeves, the targeting device received in the adjusting device is aligned and movable in a predetermined way. This predetermined movement is optionally set such that an interlocking device received in the targeting device or an instrument received in the targeting device is moveable within a cone surface. The cone tip rests thereby within the depth of that through-opening to which the interlocking device has been directed by selecting the associated sleeve into which the push-in section was inserted.

Preferably, the tip of the virtual cone or of the cone determined by calculation, rests on a longitudinal axis of the corresponding through-opening, i.e. for example in the hole center when the through-opening is seen from top.

Whenever the word cone is mentioned herein, it should not be understood as limiting. The term "cone tip" may also be understood to mean the intersection of two or several directions for introducing the interlocking device which are achievable by moving the interlocking device using the adjusting device. An actual or specific cone shape is not essential or mandatory here.

In several exemplary embodiments according to the present invention, the push-in sleeves arrangement comprises one or several of the features described herein in relation to one or several sleeves in any combination, unless such combination is recognized by the person skilled in the art as technically impossible.

The push-in sleeves arrangement according to the present invention may be used for the minimally invasive introduction of the plate to a bone.

The guiding bow may be used as aid for minimal-invasively introducing the plate on or to the bone and may be variably adjusted relative to the plate.

The guiding bow may be used for positioning and/or fixing of wires, denoted also as K-wires or Kirschner-wires, through or from one plate to a bone.

The positioning device according to the present invention comprising the connection between plate and push-in arrangement, the push-in arrangement and the guiding bow with the adjusting device may be made of materials transparent to X-rays.

Some or all of the embodiments according to the present invention may comprise one, several or all of the advantages mentioned supra and/or in the following.

With the positioning device according to the present invention, it is advantageously possible to correct, during surgery, minor misalignments when positioning and/or when screwing interlocking screws into a plate.

With the positioning device according to the present invention it is advantageously possible to correct, during surgery, misalignments of the bone by inserting an interlocking screw and subsequently by repositioning (the so-called corrective or transposition osteotomy) through or by means of the plate.

The position and the angle of bores for the interlocking screws and their positions may advantageously be adapted, still intraoperatively, to the individual anatomical situation and to an injury-caused situation by using the positioning device according to the present invention.

Furthermore, with the positioning device according to the present invention the angle of the interlocking screw penetrating or reaching through the plate may still be varied intraoperatively in order, e.g., to reposition the fracture fragments, to anatomically correctly adapt them or to reposition the bones relative to each other according to a corrective or transposition osteotomy.

By the present invention, the positioning device may be securely and simply connected, in a releasable manner, to the plate to be fixed. Thus, the positioning device may be decoupled and removed from the fixed plate. The push-in sleeves arrangement may advantageously ensure that the positioning device does not rotate, preferably not relative to the plate, during the screwing or during the release of the screw connection between bone and plate.

According to the present invention, the positioning device may enable a minimally-invasive implantation of polyaxial osteosynthesis plates. The surgeon may align the positioning device on one or several particular through-opening(s) using the push-in sleeves arrangement, even if he cannot see neither the positioning device nor the plate. The surgeon may hereby use screening (or radioscopy) or x-rays, but only if he himself chooses to do so.

Both the positioning device and the push-in sleeves arrangement may be handled intuitively. To move the positioning device within the push-in sleeves arrangement advantageously requires only one step, namely for removing the push-in section out of one sleeve and inserting it into another.

Figure 1:
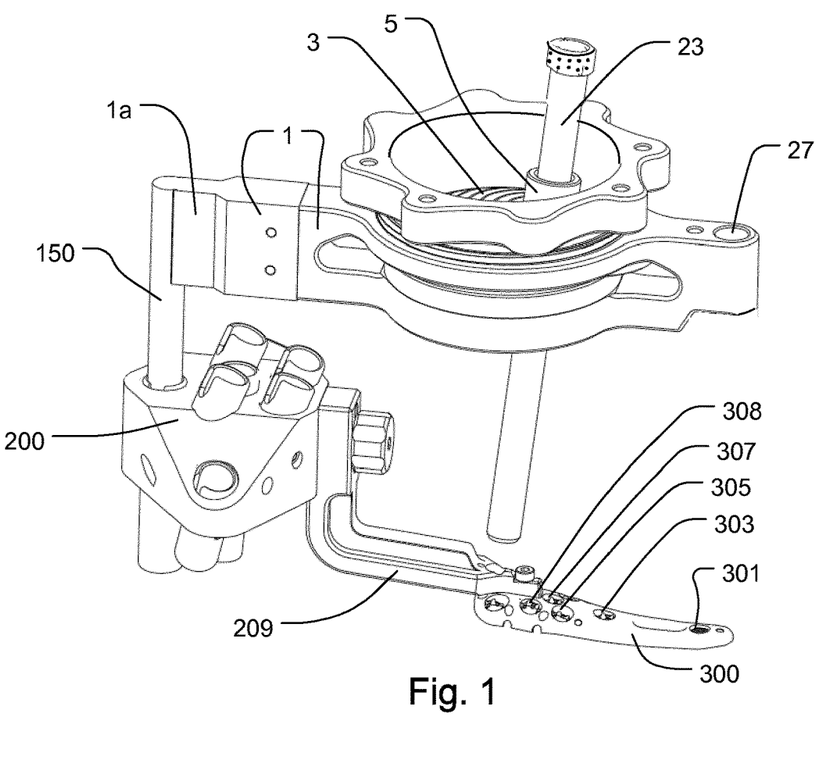
FIG. 1 shows a perspective view of a first exemplary embodiment of a positioning device according to the present invention.

The present invention is exemplarily explained with regard to the accompanying figures, in which identical reference numeral refer to the same or similar component. The following applies in the schematically simplified figures, respectively:

FIG. 1 shows a perspective view of a positioning device 100 according to the present invention of a first exemplary embodiment.

The positioning device 100 may be designed in any way disclosed in WO 2016/008849 A1, the disclosure of which is hereby incorporated by reference in its entirety.

FIG. 1 further shows a push-in sleeves arrangement 200, which is releasably connected on one hand to the positioning device 100, namely by inserting a push-in section 150 of the positioning device 100 in one of the sleeves 201, 203, 205 and 207 of the push-in arrangement 200, and on the other hand to a plate 300.

The plate 300 comprises through-openings 301, 303, 305, 307, 308 for screwing or interlocking the plate 300 to a bone.

In this, a longitudinal or rotational axis of the through-openings 301, 303, 305, 307, 308 is parallel to a longitudinal axis of at least one or exactly one of the sleeves 201, 203, 205 and 207 and possibly others, of the push-in sleeves arrangement 200.

The instrument 23 for inserting screws may selectively and depending on the desired fixing and screwing of the plate 30 on the bone be inserted into a positioning aid 17 in the guiding bow 1.

Figure 2:
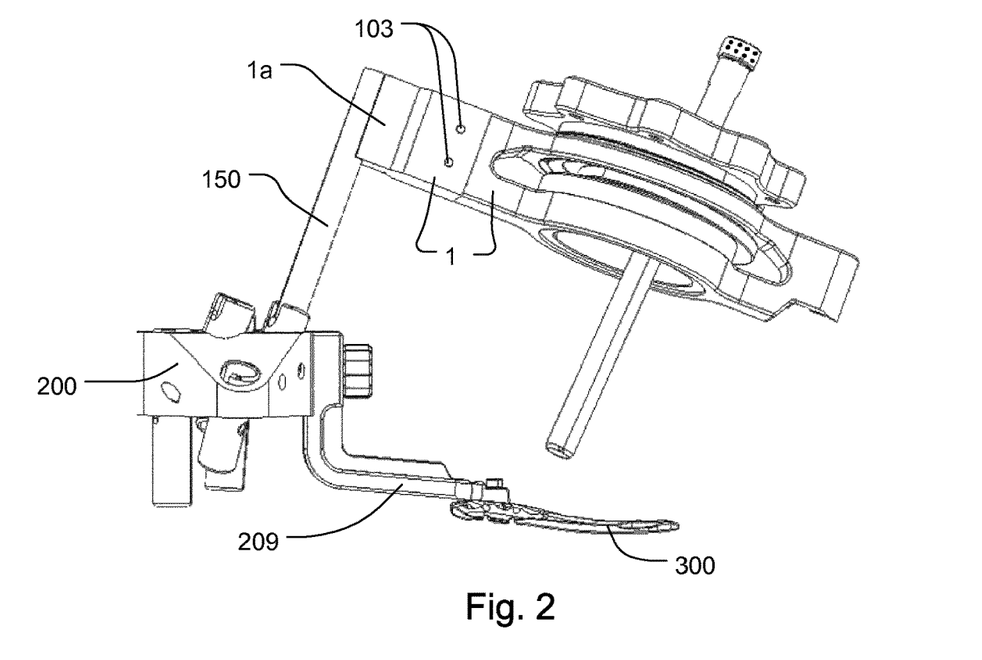
FIG. 2 shows a different perspective view of the positioning device according to the present invention of FIG. 1.

FIG. 2 shows a further perspective view of the positioning device 100 according to the present invention of FIG. 1.

Figure 3:
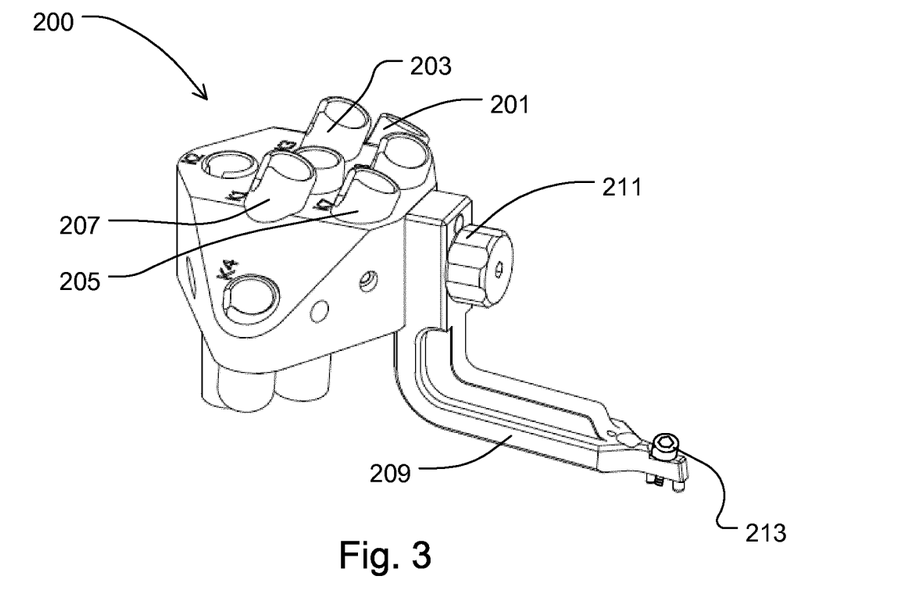
FIG. 3 shows a perspective view of a first exemplary embodiment of the push-in sleeves arrangement according to the present invention.

FIG. 3 shows a perspective view of the push-in sleeves arrangement 200 according to the present invention of a first exemplary embodiment.

Figure 4:
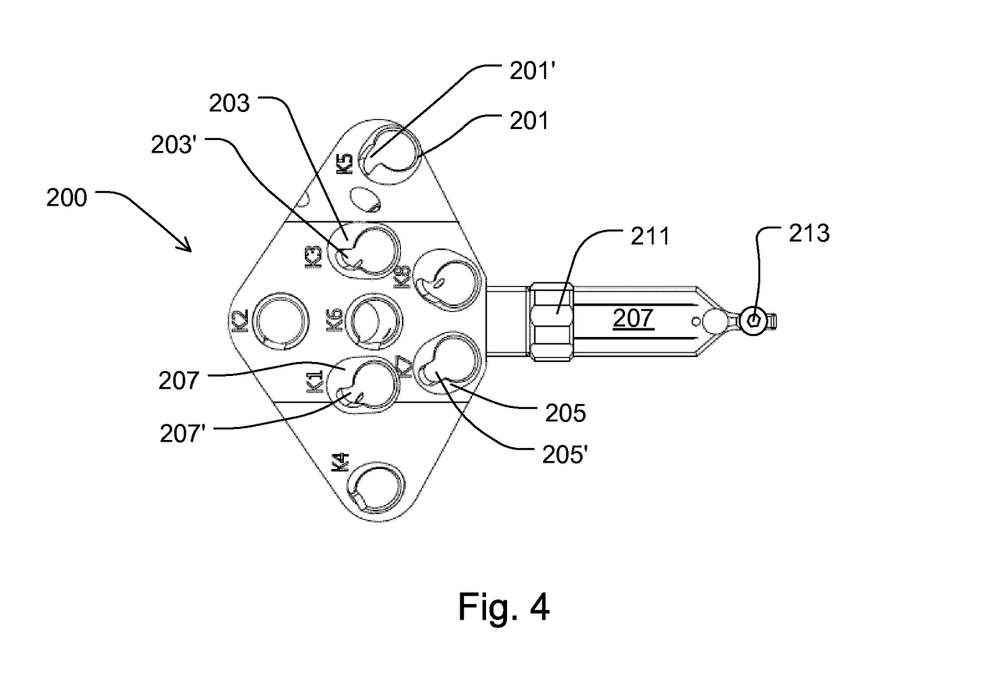
FIG. 4 shows the push-in sleeves arrangement of FIG. 3 according to the present invention from the top.

FIG. 4 shows the push-in sleeves arrangement 200 of FIG. 3 from above.

Figure 5:
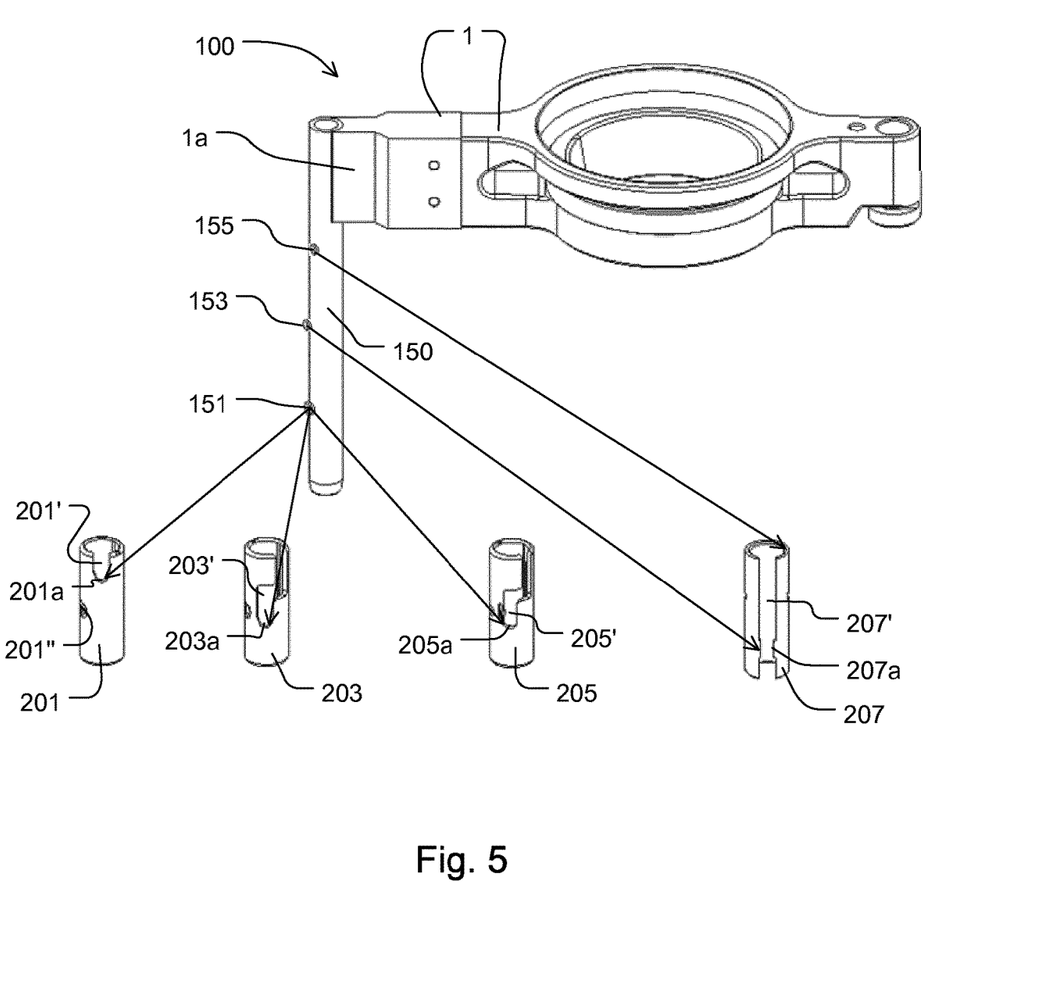
FIG. 5 shows parts of the positioning device according to the present invention of FIG. 1 as well as four sleeves.

FIG. 5 shows parts of the positioning device 100 according to the present invention of FIG. 1 as well as four sleeves 201, 203, 205 and 207.

FIG. 5 shows different options for connecting the positioning device 100 to the sleeves of the push-in sleeves arrangement (not shown in FIG. 5). Shown in FIG. 5 are only the sleeves 201, 203, 205 and 207 which may be part of the push-in sleeves arrangement 200 shown in FIG. 3.

The sleeves 201, 203, 205 and 207 comprise each a groove 201', 203', 205' and 207' which serve for receiving the guiding pins 150, 153 and/or 155 of the push-in section 150.

The groove 201', 203', 205' of the sleeves 201, 203, 205 are designed to specify the push-in section 150 by one guiding pin 151 both in its height and rotation (in each case relative to the sleeve).

For this purpose, the grooves 201', 203', 205' may each have an optional curvy course and/or an end-side fitting section 201a, 203a, 205a, or 207a, in which the guiding pin 151 may be fittingly inserted. The fitting sections 201a, 203a, 205a, or 207a on the one hand and the guiding pin 151 on the other may optionally jointly effect a centering.

The example of the sleeve 201 shows that each sleeve may comprise at least one opening 201' for receiving at least one fitting pin by which the sleeve may be fixed and/or aligned on the push-in sleeves arrangement 200.

The example of the sleeve 207 however shows that the height and rotation angle of the push-in section 150 may be ensured by more than only one guiding pin. The groove 207' which comprises a fitting section 207a may, using a guiding pin 153, protect against an undesired rotation. A second guiding pin 155 may prevent the push-in section 150 from being inserted too deep into the sleeve 207 e.g. by or due to resting on the upper edge of the sleeve 207. Alternatively, the second guiding pin 155 may contact the sleeve 207 or be connected thereto in a different way.

Figure 7:
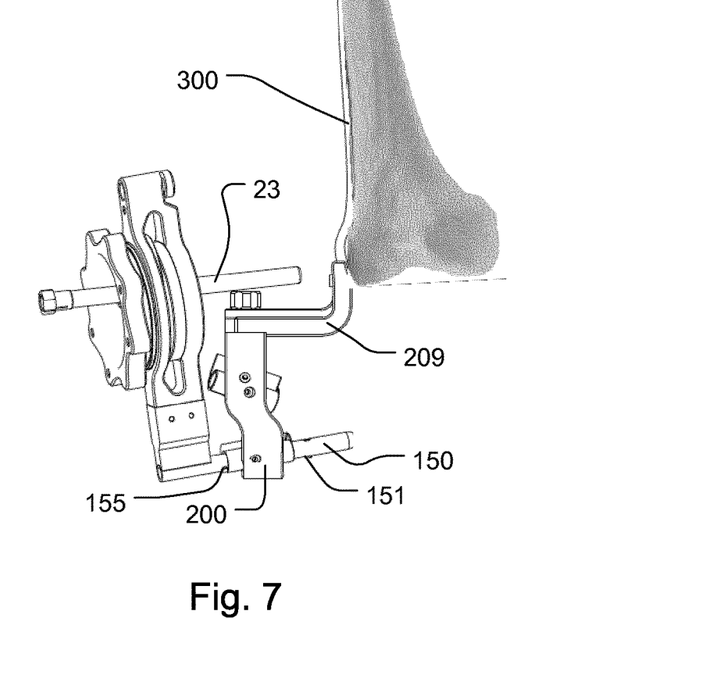
FIG. 7 shows the positioning device according to the present invention of FIG. 6 substantially from the side.

As is not only seen in FIG. 7, the groove 207a which is open at the bottom and the width of which is larger than the thickness of the guiding pin 151, may allow a pushing or an insertion of the guiding pin 151 through the fitting section 207a. Only the guiding pin 153 may not be pushed through the fitting section 207a. In this way, the push-in section 150 may be inserted into the sleeve 207 relatively very deep, which is not possible with other sleeves, e.g. with the sleeve 201. This design allows a great flexibility regarding the distance of the positioning device 100 from the plate 300.

Figure 6:
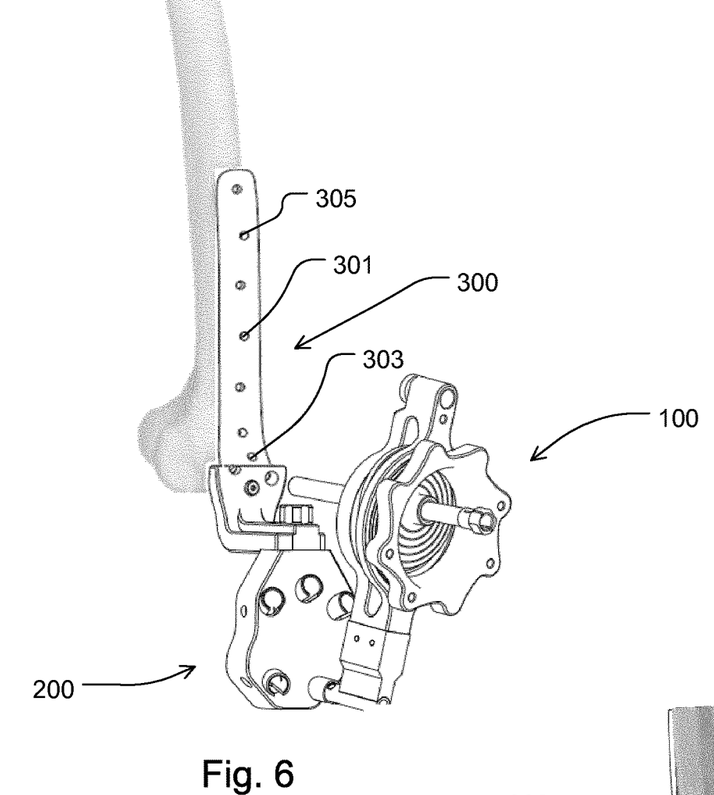
FIG. 6 shows a perspective view of the positioning device according to the present invention of FIG. 1 connected to a plate.

FIG. 6 shows a perspective view of the positioning device according to the present invention of FIG. 1 connected to a plate 300.

FIG. 7 shows the positioning device from FIG. 6 substantially from the side.

Figure 8:
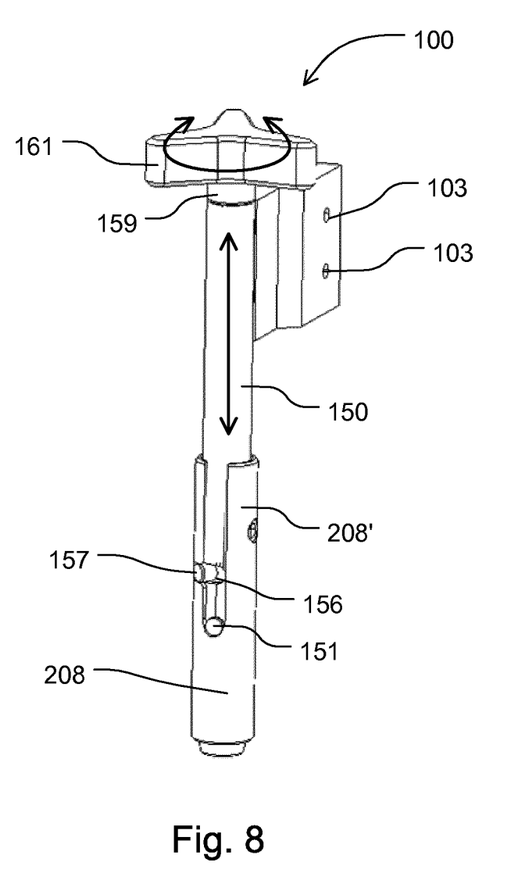
FIG. 8 shows a push-in section for a positioning device according to the present invention of a second embodiment.

FIG. 8 shows a push-in section 150 for positioning device 100 according to the present invention of a second embodiment.

In FIG. 8, the push-in section 150 comprises in addition to the guiding pin 151 which is known from the preceding figures, a further guiding pin 157. The latter protrudes from an outer surface or a circumferential surface of the push-in section 150 and it is connected optionally rotation-free to a rod 159 lying in the interior of the push-in section 150. If the rod 159 is turned or rotated in arrow direction using the optional hand element 161, then the guiding pin 157 will lock the push-in section 150 in the section 208b extending in circumferential direction of the groove 208' of the sleeve 208. In this way, it prevents the push-in section 150 from slipping out due to simple movement or undesired rotation of the positioning device 100.

Figure 9:
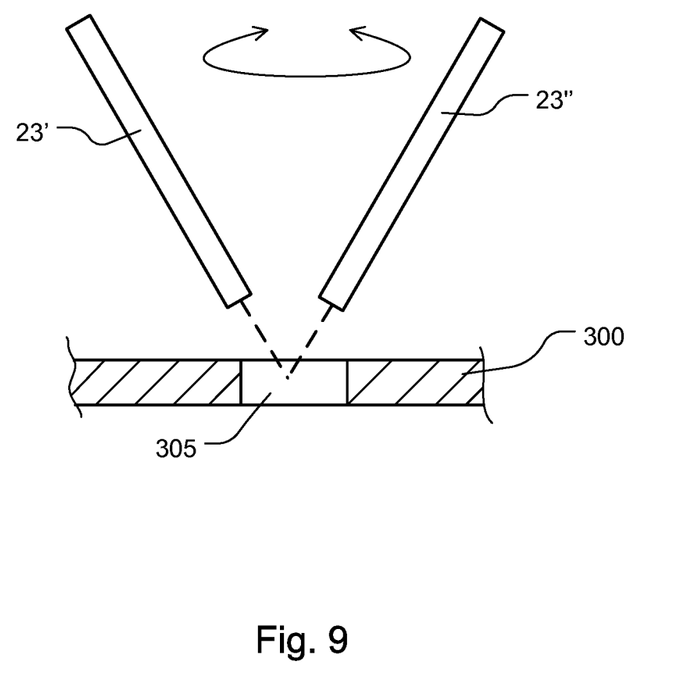
FIG. 9 shows a schematic view of the alignment between positioning device and plate in an exemplary embodiment according to the present invention.

FIG. 9 shows a schematic view of the alignment between the positioning device and plate in an exemplary embodiment according to the present invention. The alignment is such that the instrument 23 (or any other tool which is guided through the targeting device 5, not shown in FIG. 9) may be moved following the shape of a cone between end positions, from which two end positions 23' and 23" are shown.

The tip or head of the cone should thereby rest, as shown by dashed lines, in the thickness of the plate 300 which is shown here in section from the side, or in one of the openings 305 for the interlocking device which is not shown.

Figure 10:
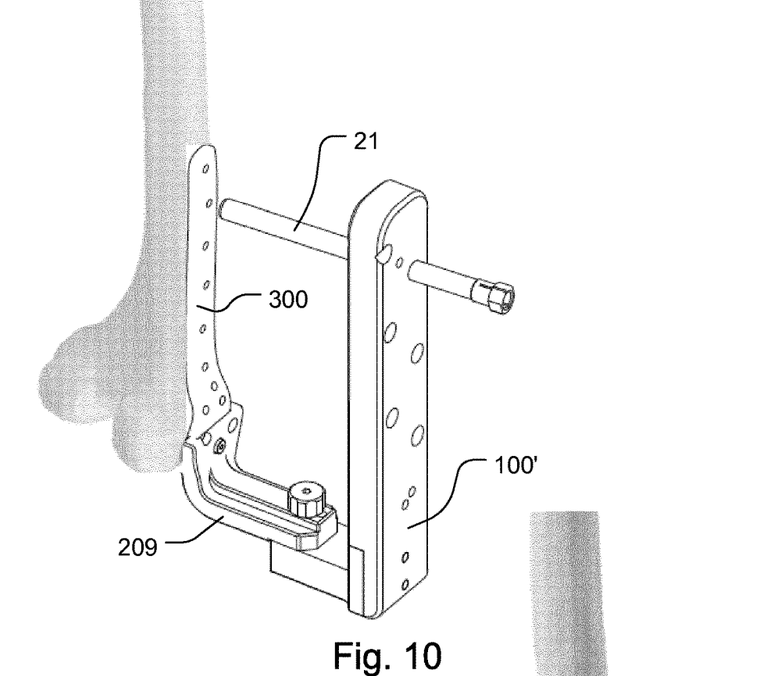
FIG. 10 shows a perspective view of the plate holder from FIG. 6 or 7 connected to a monoaxial positioning device.

FIG. 10 shows a perspective view of the plate holder 209 of FIG. 6 or 7 connected to a monoaxial positioning device 100'.

Figure 11:
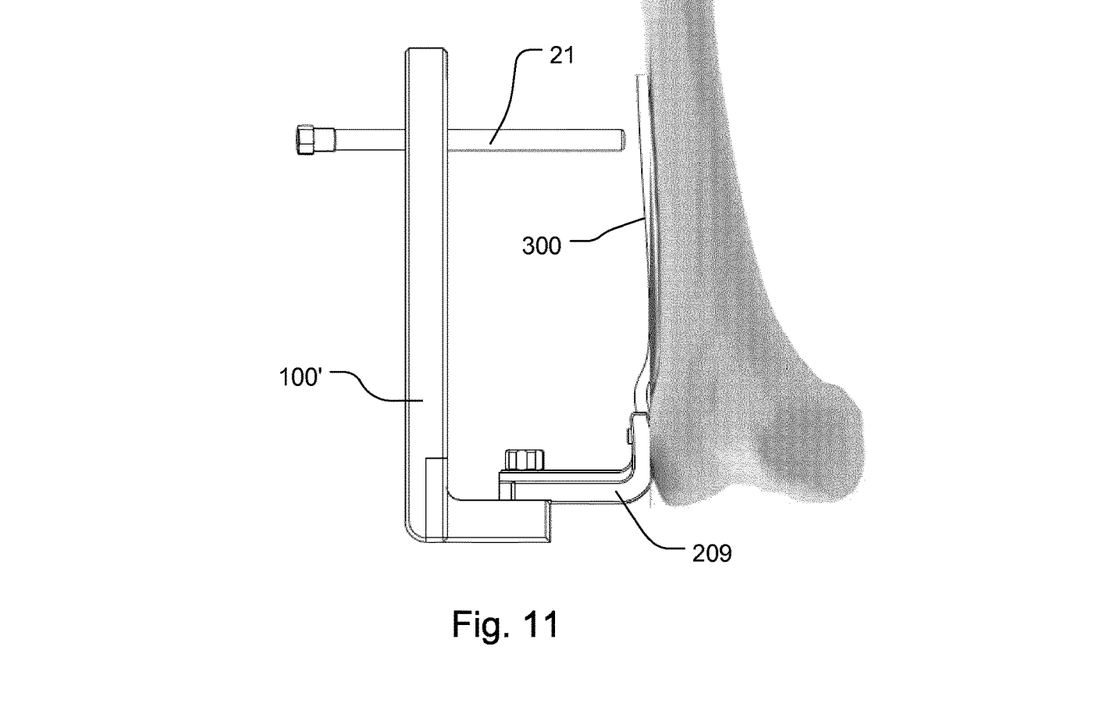
FIG. 11 shows a side view of the plate holder of FIG. 10 being connected.

FIG. 11 shows a side view of the plate holder 209 of FIG. 10.

The embodiment may relate to a set having or consisting of the polyaxial positioning device 100 and/or the monoaxial positioning device 100', the push-in sleeves arrangement 200, the plate holder 209 and optionally one or several plates 300.

Figure 12:
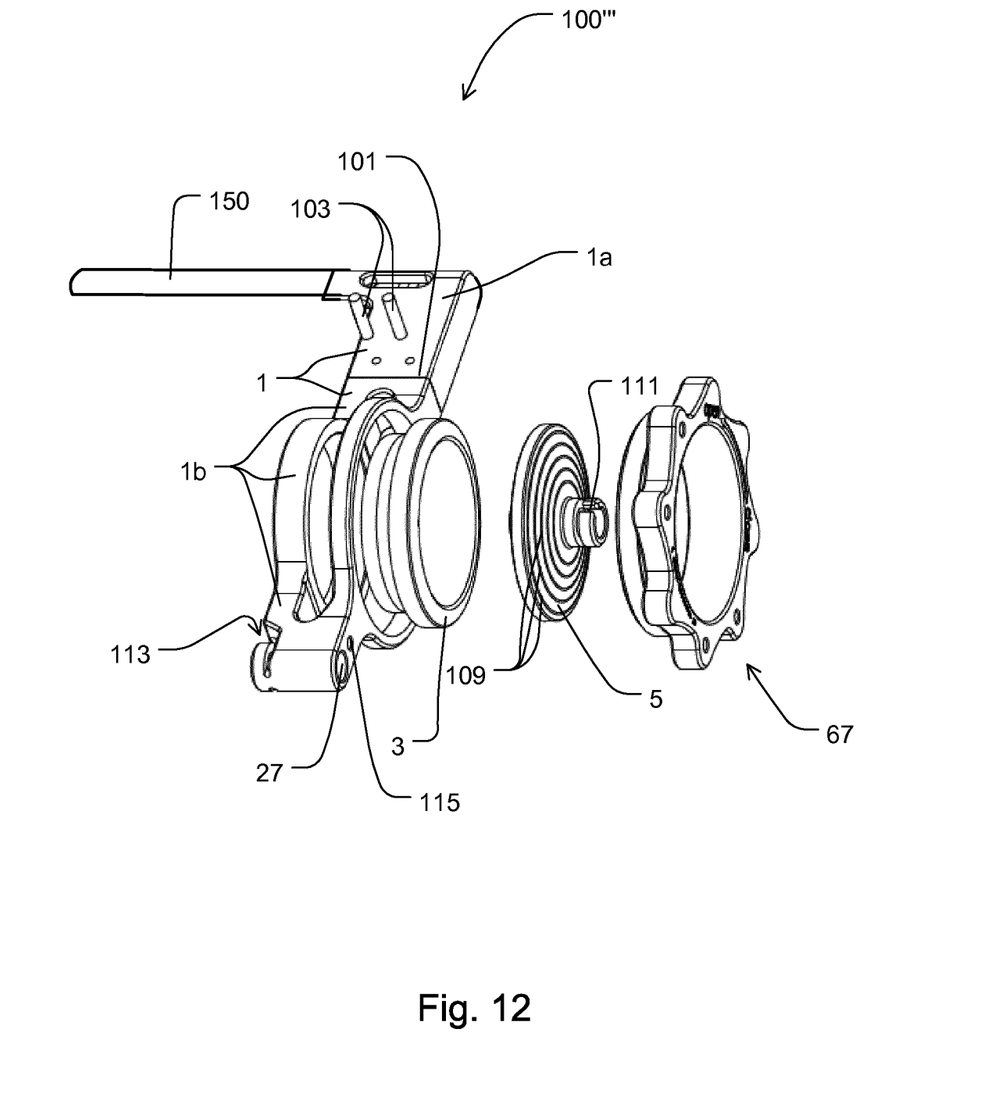
FIG. 12 shows a further embodiment of a positioning device according to the present invention.

FIG. 12 shows a further embodiment of a positioning device 100" according to the present invention.

The adjusting device 3 is designed optionally as a section of a spherical surface with a circular or round opening. The form of the adjusting device 3 may comprise instead of a spherical surface likewise a different shaped surface, only optionally curved or straight.

The adjusting device 3 is optionally fixed to the guiding bow 1.

The exemplary circular opening in a central or middle area of the adjusting device 3 is provided for guiding the targeting device 5 and the instrument 23 (which serves for inserting the interlocking screw 21). The longitudinal axis of the instrument 23 is perpendicular to the spherical surface. The extension of the longitudinal axis of the instrument 23 extends through the center of a bore or a through-opening of the plate 300.

The instrument 23 is guided to the targeting device 5. The targeting device 5 is optionally shell-like formed having grooves, notches or protrusions which are annularly concentrically arranged about the middle guide of the instrument 23. The shell-like formed targeting device 5 may be referred to as middle shell, which, viewed in the radial direction, is arranged between the outer shell which corresponds to the adjustment device 3 and the inner shell which corresponds to the shell-shaped fitting surface of the guiding bow 1.

The targeting device 5, i.e. the middle shell, may be moved or shifted between the inner and the outer shell. In this movement, optional pins (not shown), supported in radial direction by springs, engage in the annular grooves or notches of the targeting device 5. A defined and exact positioning of the instrument 23, and thus of the interlocking screw 21, is thus possible. The distances between the grooves correspond to a specific and predetermined deflection of the targeting device 5, which may be indicated with an angle or degree number. In this embodiment, the deflection between two annular grooves corresponds to an angle or a degree number of degree (1°). This principle or concept with pins supported by springs in which these pins engage into grooves, may be referred to as spring-pin concept.

The arrangement in FIG. 12 allows a deflection of the instrument 23 (and thus of the interlocking screw 21) by a desired or predetermined degree (or degree range), for example of ten degrees (10°), compared to the centrical initial position in the middle (this initial position is shown in FIGS. 7, 10 and 11 and is referred to as zero-degree position (0°)).

With an optional combined form-fit connection (between the pins and the annular grooves of the targeting device 5) and a frictional connection (between the middle and the outer shell), fixing the position of the instrument 23 for screwing in or fixing the interlocking screw 21 is, hence, possible.

The targeting device 5 may optionally rest on a circular section of a structure which is arranged under the targeting device 5. In this way, it may be ensured that the targeting device 5 is preferably guided at a constant distance from a target point.

The targeting device 5 is fixed between the adjusting device 3 and the second section of the guiding bow 1 by a so-called tension wheel 67.

The targeting device 5 may comprise markings, e.g. the exemplarily shown concentric rings 109, on at least one surface which is shown as an option in FIG. 12. These optional purely optical rings 109 which may alternatively or additionally be raised (or lowered) serve the user for optically and/or haptically orienting the actual positioning of the targeting device 5, which is arranged to be shiftable between the tension wheel 67 and the adjusting device 3.

As an alternative or in addition to the concentric rings 109, a mechanical aid may be provided for the doctor, e.g. a snap-in device that gives a feedback for a snap-in being noticeable in the hand for a predetermined angular position, e.g. 0°. Such an optical or haptical orientation may be helpful when using monoaxial plates or in monoaxial implantation.

The mechanical aid may be a groove in which a pin passes or enters, or the like.

The guiding bow 1 is optionally two-piece. A first section 1a (in FIG. 12 above) is connected to a second section 1b, in particular releasably. Alternatively, the connection may be a non-releasable material-bonding connection, for example a soldered connection, a welded connection or an adhesive connection. The material-bonding, integral connection, may be a one-piece component, e.g., made of a material by casting and/or machining. The first section 1a may be produced by a generative production method, e.g., by a laser sintering method or a rapid prototyping method.

A second section 1b of the guide bow 1 may be produced as one-part or multi-part.

The first section 1a and the second section 1b may be connected to each other at an interface 101 by means of a form-fit and/or material-bonding connection. For example, the second section 1b may be form-fit or positively pushed into a hollow end section of the first section 1a by a step. This form-fit connection may then be fixed and secured by one or several bolts 103 (the bolts 103 may be dowel pins). This form-fit connection may be additionally secured by an adhesive sealing. An adhesive sealing may be advantageous in order to ensure a play-free connection even after prolonged use and multiple mechanical stresses. A play-free connection may be important for a therapeutic success of an exact positioning and/or fixing of plates 300 by the positioning device 100" according to the present invention.

The tension wheel 67 connects and fixes, in the mounted state, optionally the targeting device 5 and the adjusting device 3 to the guiding bow 1. The exemplary tension wheel 67 is explained in detail in FIG. 13.

The targeting device 5 comprises the concentric rings 109 on at least one surface (on the right side in FIG. 12). These optional optical and/or haptical rings serve the user to control or orient the current positioning of the targeting device 5, which is arranged movable between the tension wheel 67 and the adjusting device 3.

Furthermore, the targeting device 5 comprises a longitudinal slot 111 on the circumference of the centrical, sleeve-shaped protrusion. This longitudinal slot 111 serves for an elastic deformation of the annular protrusion when inserting an instrument for inserting the interlocking screw 21 (see FIG. 1). In the non-deformed state, the inner diameter of the protrusion is slightly smaller than the diameter of the instrument 23. The protrusion is elastically deformed and widened during the insertion of the instrument 23 and can subsequently be actively moved or rotated, by effort or force, against the frictional resistance between the protrusion and the instrument. Due to the frictional resistance, the instrument can only be actively moved, but cannot fall out or decouple. This type of clamping is advantageous when the instrument 23 cannot be permanently manually fixed and held, but still should remain in a predetermined position.

The second section 1b of the guide bow 1 comprises an optional positioning aid 27 as a bore for further instruments (not shown) for inserting interlocking screws. This positioning aid 27 comprises also a longitudinal slot 113 (hidden) at one end (in FIG. 12 left), which has the same function as the longitudinal slot 111. Thus, an instrument 23 which is pushed into the bore of the positioning aid 27 is movable on the one hand but is clamped on the other hand due to the frictional resistance to prevent it from falling out or from decoupling.

Furthermore, the second section 1b comprises an optional bore 115 for a connecting pin, in particular for a dowel pin. With this dowel pin, the second section 1b can be connected in particular to an extension (not shown in FIG. 12) in order to provide for example further bores for positioning aids for inserting further interlocking screws into the plate 300.

The components shown in FIG. 12 may be made of one or several different materials. Preferably, the components second section 1b, adjusting device 3, targeting device 5 and the tension wheel 67 are made of a plastic; the remaining components are made of one or different metallic materials. Only by way of example, the plastic components may be made of, or comprise, one or different types of the following plastics: PEEK (polyetheretherketone); PEEK fiber reinforced; PEEK fiber reinforced in different concentrations of fibers; polyoxymethylene (POM); carbon fiber reinforced plastic (CFRP), polyarylsulfone, in particular polyphenylsulfone (PPSU). Only by way of example, the components made of metal are made of stainless steel or comprise such a material. The stainless steel can be hardened and/or blasted.

Figure 13:
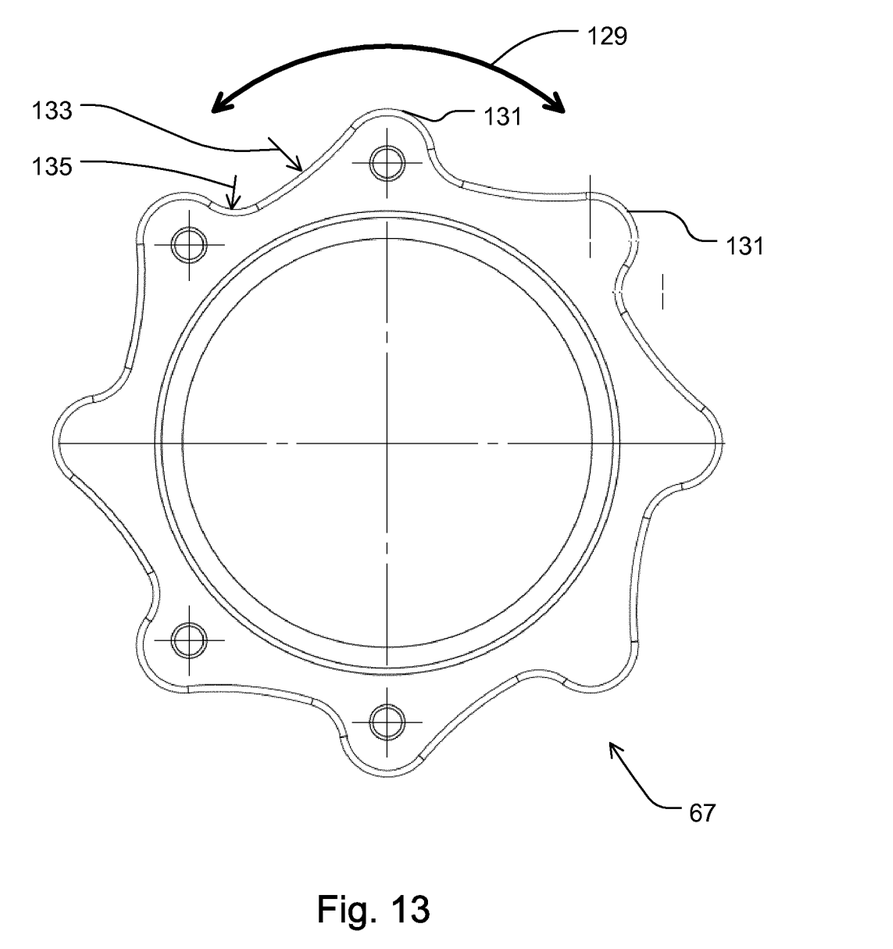
FIG. 13 shows a tension wheel for the positioning device according to the present invention.

FIG. 13 shows a further tension wheel 67. In this embodiment, the tension wheel 67 has asymmetrical engagement contours or peripheral or external contours for, in particular manual, tightening and releasing.

The optional asymmetrical engagement contour of FIG. 13 may be referred to as a sawtooth contour. The tension wheel 67 is, e.g., tightened clockwise (with regard to the top view in FIG. 13) of the direction of rotation 129 and is released counterclockwise. For this operation, the flank in clockwise direction is much flatter than the flank for release. In this, only a small amount of torque can be applied for tightening. If the torque is increased too much, the hand or the fingers in contact slip beyond the nubs 131 during manual tightening by the user. In this way, it can advantageously be achieved that no too high torques may be applied for tightening the tension wheel. Very high torques could cause damage or breaking of this component which is preferably made of plastic. Preferably, in the present embodiment, it is simpler to apply torque to the tension wheel for releasing than for tightening. The user can therefore be sure to be able to release the previously manually tightened tension wheel with his own strength by hand.

Still, a tool can be used alternatively to a pure manual actuation of the tension wheel 67.

The different inclinations of the flanks are defined by the radii 133 and 135. The radius 133 may be approximately 6 mm and the radius 135 may be approximately 49 mm, by way of example.

Figure 14A:
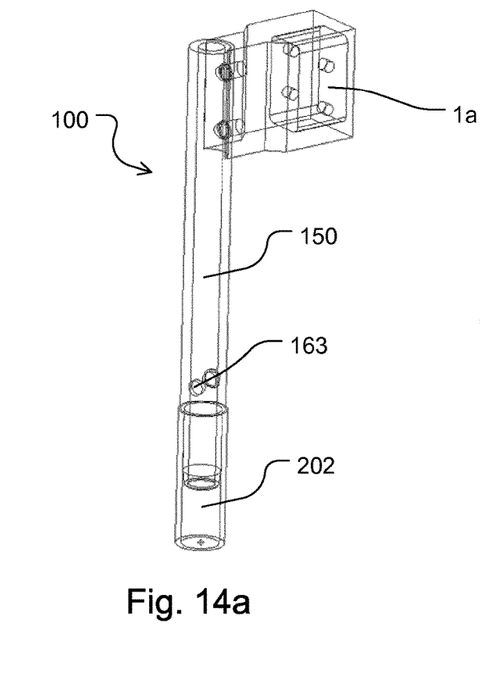
FIG. 14a shows a push-in section for a positioning device according to the present invention of a third embodiment.

FIG. 14a shows a third embodiment of a push-in section 150 for a positioning device 100 according to the present invention. The longitudinal axes of the cylindrical sleeve 202 and the push-in section 150 are identical in this embodiment. The sleeve 202 is placed on the push-in section 150, e.g. by a fitting between the outer diameter of the sleeve 202 and the inner diameter of the push-in section 150.

In order to prevent a mutual twisting of the push-in section 150 and the sleeve 202, a pin, a dowel pin, a notch may be arranged in a step or the like thereto preferably on the outer diameter of the push-in section 150 and on the inner diameter of the sleeve 202.

In order to limit the axial shiftability of the sleeve 202 on the push-in section 150, a pin or the like may be inserted in optional cross bores 163 of the push-in section 150. Such a pin may be understood as an axial stop for the sleeve 202. With such an axial stop, the height or distance of the instrument 23 with regard to the plate 300 may be adjusted or set (see FIG. 7).

Figure 14B:
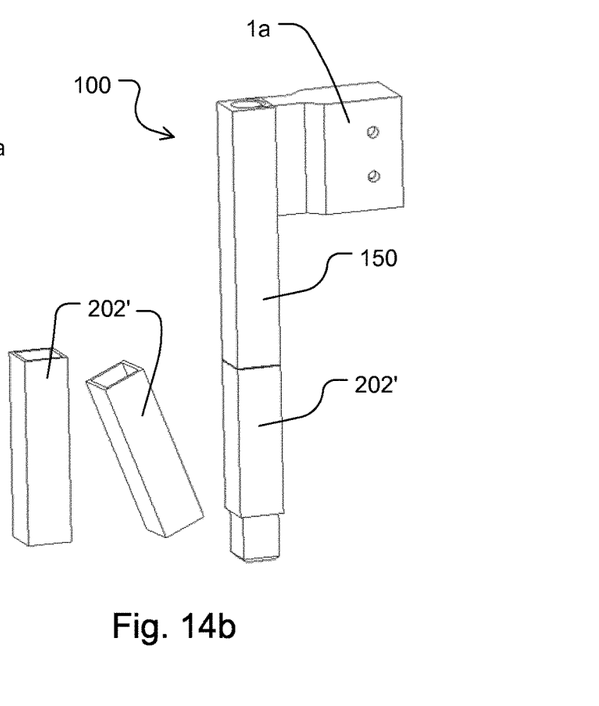
FIG. 14b shows a push-in section for positioning device according to the present invention of a further embodiment having angular sleeves.

FIG. 14b shows a further embodiment of an angular push-in section 150 for the positioning device 100 according to the present invention having angular sleeves 202'. The sleeves 202' may optionally have different lengths for the adjustment or setting of the height (see the description of FIG. 14a).

Figure 14C:
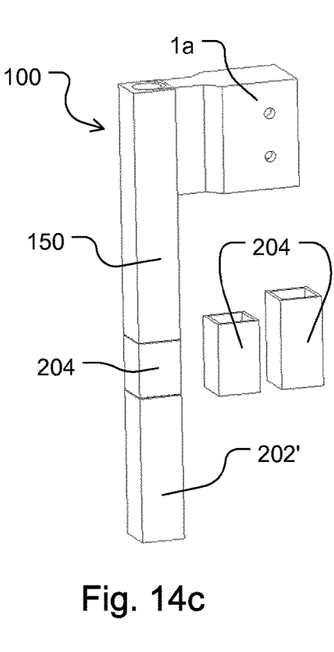
FIG. 14c shows a push-in sleeve for a positioning device according to the present invention of further embodiment having intermediate sleeves.

FIG. 14c shows a further embodiment of an angular push-in section 150 analogue to the embodiment of FIG. 14b for a positioning device 100 according to the present invention having intermediate sleeves 204. Using one or several intermediate sleeves 204, the height may be adjusted (see the description of FIG. 14a).

Figures 14D, 14E:
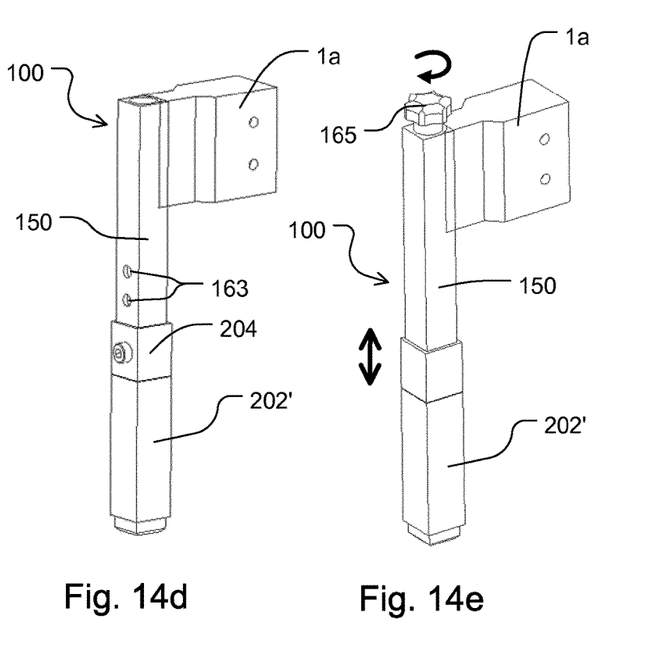
FIG. 14d shows a push-in section for a positioning device according to the present invention of a further embodiment having a lockable intermediate sleeve.
FIG. 14e shows a push-in section for a positioning device according to the present invention of a further embodiment having a locking device.

FIG. 14d shows a further embodiment of an angular push-in section 150 for a positioning device 100 according to the present invention having a lockable intermediate sleeve 204. The intermediate sleeve 204 may be axially fixed by a pin through the step externally on the intermediate piece 204 and the cross bores 163.

FIG. 14e shows a further embodiment of an angular push-in section 150 for a positioning device 150 according to the present invention having a locking device 165. The locking device 165 may be fixed and released through turning so that e.g. by a cone arranged inside (in the push-in section 150 and in the sleeve 202') the sleeve 202' may be axially fixed.

Figure 15:
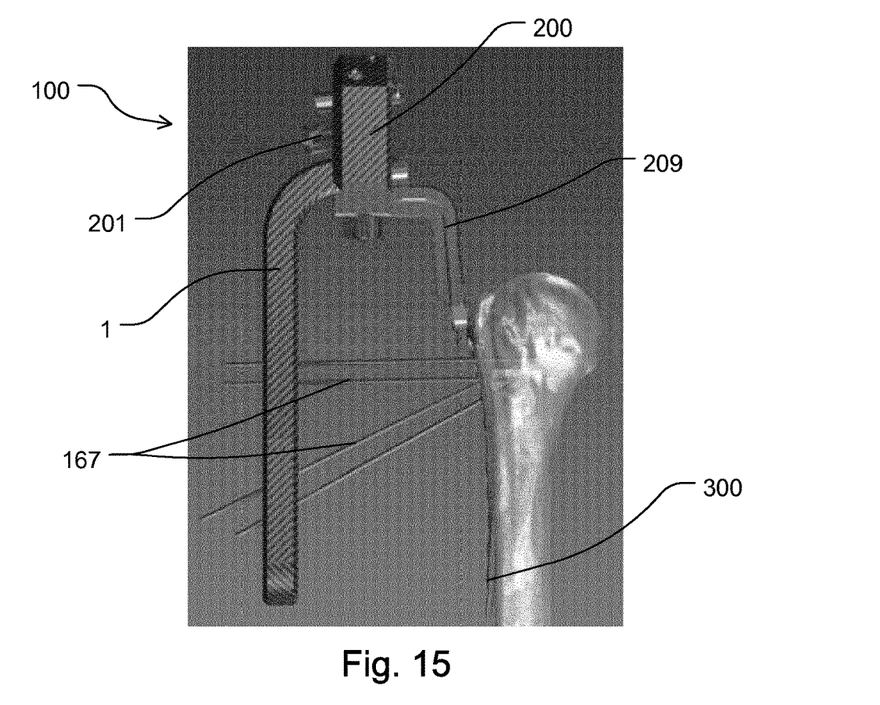
FIG. 15 shows a side view of the positioning device according to the present invention for guiding K-wires.

FIG. 15 shows a side view of the positioning device 100 according to the present invention for guiding K-wires (Kirschner wires). Using the K-wires, the plates 300 may be fixed to the bone after bone fractures.

The plate 300 fixed to the bone is connected to a plate holder 209. This connection may be a screw connection, a form-fit connection and/or a frictional connection. The connection may comprise a predetermined breaking point so that after a positioning and fixing of the plate 300 to the bone, the plate holder 209 may be bent off and thus broken off and advantageously detached from the plate 300 easily and quickly.

The plate holder 209 is connected to a push-in sleeves arrangement 200, e.g. by a screw connection. The push-in sleeves arrangement 200 comprises several sleeves 201, in which the guiding bow 1, depending on the desired positioning, may be inserted. With this positioning, the position of the guiding bow 1 is fixed relative to the plate 300 and to the bone. Subsequently, the K-wires for bone fixation may be inserted.

Figure 16:
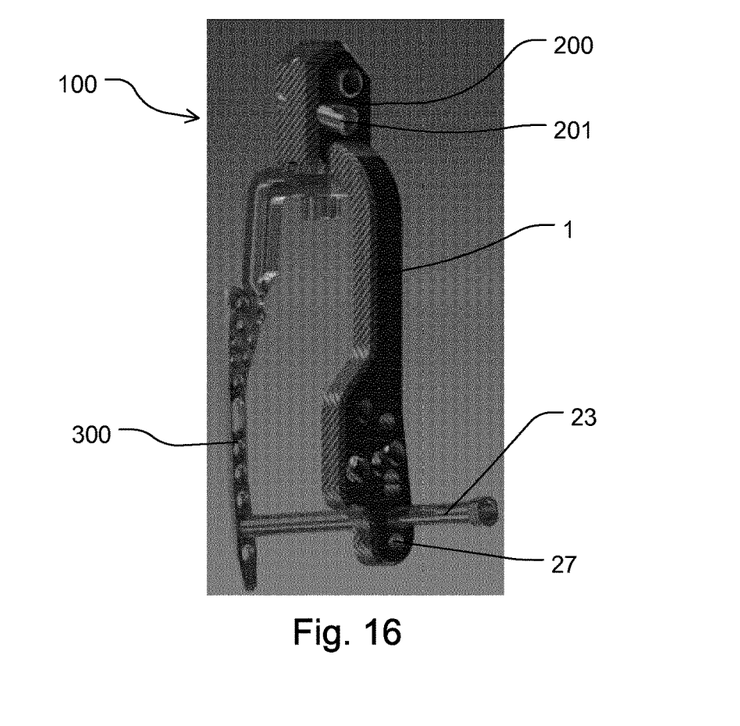
FIG. 16 shows a further embodiment of a positioning device according to the present invention.

FIG. 16 shows a further embodiment of the positioning device 100 according to the present invention. Unlike in the embodiment of FIG. 15, in FIG. 16, no K-wires for bone fixation are inserted in the guiding bow 1, rather instruments 23. With such a kind of instruments 23, the screws for fixing the plate 300 to the bone may be screwed. The instruments 23 are selectively and depending on the desired fixation and screwing of the plate 300 to the bone inserted in one of the pre-drilled positioning aids 27 in the guiding bow 1.

| List of reference numerals | |
|---|---|
| 1 | guiding bow |
| 1a | first section |
| 1b | second section |
| 3 | adjusting device |
| 5 | targeting device |
| 21 | interlocking device |
| 23 | instrument |
| 27 | positioning aid |
| 67 | tension wheel |
| 100, 100', 100" | positioning device |
| 101 | interface |
| 103 | bolts or pins |
| 109 | concentric rings |
| 111 | longitudinal slot |
| 113 | longitudinal slot |
| 129 | rotation direction |
| 131 | nubs |
| 133 | radius |
| 135 | radius |
| 150 | push-in or plug-in section |
| 151 | guiding pin |
| 156 | through-opening |
| 157 | guiding pin |
| 159 | rod |
| 161 | hand element |
| 163 | cross bore |
| 165 | locking device |
| 200 | push-in or plug-in sleeve arrangement |
| 201, 203, 205, 207, 208 201" | sleeves |
| 201', 203', 205', 207', 208' | longitudinal groove |
| 201a, 203a, 205a, 207a | fitting or mating sections |
| 204 | intermediate sleeve |
| 208b | circumferential section |
| 209 | plate holder or plate support |
| 211 | first connection |
| 213 | second connection |
| 300 | plate |
| 301, 303, 305, 307, 308 | through-openings |

The invention claimed is:

1. A positioning device for positioning and/or fixing a plate to a bone, comprising:
   a push-in sleeves arrangement; and
   a guiding bow, wherein the guiding bow is designed at least in one section thereof as a push-in section to be inserted into a sleeve of the push-in sleeves arrangement or comprises or is connected to such push-in section;
   wherein the guiding bow one of comprises and is connected to:
     an adjusting device, wherein the adjusting device comprises at least one targeting device, and wherein the at least one targeting device is designed to at least partially receive an interlocking device or an instrument for acting on the interlocking device, wherein the adjusting device comprises an opening for guiding the targeting device and the instrument,
   the push-in sleeves arrangement having a plurality of sleeves for the insertion of the push-in section of the guiding bow wherein the sleeves comprise each a longitudinal axis, and wherein not all of the longitudinal axes of the sleeves are parallel to each other, the push-in sleeves arrangement being configured to receive the push-in section of the guiding bow.

2. The positioning device according to claim 1, wherein the push-in sleeves arrangement comprises a plate holder which is connected thereto, wherein the plate holder extends from the push-in sleeves arrangement.

3. The positioning device according to claim 2, wherein the plate holder comprises a first connection for its releasable connection to a further section of the push-in sleeves arrangement.

4. The positioning device according to claim 2, wherein the plate holder comprises a second connection for its connection to the plate.

5. The positioning device according to claim 1, wherein the push-in section comprises at least one guiding pin extending radially therefrom for guiding the push-in section into a longitudinal groove which is embodied in each one of the plurality of sleeves.

6. The positioning device according to claim 1, wherein each of the plurality of sleeves comprises at least one longitudinal groove.

7. The positioning device according to claim 6, wherein the longitudinal groove does not extend over the whole length of the sleeve and/or wherein a width of the longitudinal groove is not constant over the whole length of the sleeve.

8. The positioning device according to claim 6, wherein the longitudinal groove at least partially is provided in the circumferential direction of the sleeve.

9. The positioning device according to claim 6, wherein the longitudinal groove comprises at least one fitting section which provides a predetermined fit with at least one guiding pin.

10. The positioning device according to claim 1, wherein the plurality of sleeves are marked by markings on the push-in sleeves arrangement.

11. The positioning device according to claim 1, wherein the plurality of sleeves is either screwed, fitted, glued, or connected by dowel pin to other sections of the push-in sleeves arrangement.

12. The positioning device according to claim 1, wherein the push-in section comprises in its outer surface or shell surface a through-opening for guiding through a guiding pin, wherein the push-in section comprises in an interior thereof at least one longitudinal opening, wherein a rod is rotatably arranged in the interior or in the longitudinal opening, the rod having the guiding pin on its outer surface or protruding from its outer surface, wherein the guiding pin is led through the through-opening.

13. The positioning device according to claim 12, wherein the rod comprises a hand element for rotating or turning the rod within the longitudinal opening of the push-in section by hand.

14. The positioning device according to claim 1, connected to the push-in sleeves arrangement, wherein the push-in sleeves arrangement is connected to the plate for osteosynthesis, wherein the plate comprises a plurality of through-openings for receiving one or several of the interlocking devices, wherein the depth of the through-openings respectively corresponds to a thickness of the plate, wherein each of the plurality of the sleeves respectively corresponds to one of the through-openings, wherein, with the push-in section being inserted into one of the sleeves the adjusting device is designed or arranged such that the targeting device is aligned and is movable such that the interlocking device received in the targeting device or an instrument received in the targeting device is movable, in particular following or according to the shape of a cone surface within the cone surface, wherein a cone head rests within the depth of the through-opening of the sleeve in which the push-in section is inserted.

15. The push-in sleeves arrangement according to claim 1, wherein each of the plurality of sleeves comprises at least one longitudinal groove.

* * * * *